(12) United States Patent
Osborne

(10) Patent No.: US 9,131,644 B2
(45) Date of Patent: Sep. 15, 2015

(54) CONTINUAL CROP DEVELOPMENT PROFILING USING DYNAMICAL EXTENDED RANGE WEATHER FORECASTING WITH ROUTINE REMOTELY-SENSED VALIDATION IMAGERY

(71) Applicant: ITERIS, INC., Santa Ana, CA (US)

(72) Inventor: Leon F. Osborne, Grand Forks, ND (US)

(73) Assignee: ITERIS, INC., Santa Ana, CA (US)

( * ) Notice: Subject to any disclaimer, the term of this patent is extended or adjusted under 35 U.S.C. 154(b) by 0 days.

(21) Appl. No.: 14/463,111

(22) Filed: Aug. 19, 2014

(65) Prior Publication Data

US 2014/0358486 A1    Dec. 4, 2014

(51) Int. Cl.
*G06G 7/48* (2006.01)
*A01G 7/00* (2006.01)
*G06F 17/50* (2006.01)

(52) U.S. Cl.
CPC .............. *A01G 7/00* (2013.01); *G06F 17/5009* (2013.01)

(58) Field of Classification Search
CPC ......... G01V 1/00; A01G 7/00; G06F 17/5009
USPC ............................................................ 703/6
See application file for complete search history.

(56) References Cited

U.S. PATENT DOCUMENTS

| 7,058,197 | B1 * | 6/2006 | McGuire et al. | 382/100 |
| 7,974,853 | B1 * | 7/2011 | Zimmerman | 705/1.1 |
| 2002/0183935 | A1 * | 12/2002 | Skinner | 702/19 |
| 2005/0283314 | A1 * | 12/2005 | Hall | 702/2 |
| 2009/0150000 | A1 * | 6/2009 | Stelford et al. | 700/284 |

FOREIGN PATENT DOCUMENTS

WO    WO 2013/128557 A1 *  6/2013  ............. G06Q 50/02

OTHER PUBLICATIONS

Hirufumi Nakazaki, "Cost Calculation method, Cost Calculation Program, and Cost Calculation Device" Pro-Quest Machine Translation of WO 2013/128557, translated on Dec. 18, 2014, 65 pages.*
Andrew J. Challinor, Frank Ewert, Steve Arnold, Elisabeth Simelton, Evan Fraser, "Crops and climate change: progress, trends, and challenges in simulating impacts and informing adaptation" Journal of Experimental Botany, vol. 60, No. 10, published Mar. 16, 2009, pp. 2775-2789.*

* cited by examiner

*Primary Examiner* — Dwin M Craig
(74) *Attorney, Agent, or Firm* — Lazaris IP

(57) ABSTRACT

A modeling framework for estimating crop growth and development over the course of an entire growing season generates a continuing profile of crop development from any point prior to and during a growing season until a crop maturity date is reached. The modeling framework applies extended range weather forecasts and remotely-sensed imagery to improve crop growth and development estimation, validation and projection. Output from the profile of crop development profile generates a combination of data for use in auxiliary farm management applications.

28 Claims, 2 Drawing Sheets

CONTINUAL CROP DEVELOPMENT PROFILING USING DYNAMICAL EXTENDED RANGE WEATHER FORECASTING WITH ROUTINE REMOTELY-SENSED VALIDATION IMAGERY

FIELD OF THE INVENTION

The present invention relates to crop development profiling in precision agriculture. Specifically, the present invention relates to a system and method of augmenting growing degree day models with dynamical extended range weather forecasts and routine remotely-sensed validation imagery for developing profiles of crop growth throughout a crop growing season.

BACKGROUND OF THE INVENTION

The relationship between weather and plant growth has been recognized for many centuries. For example, the importance of inter-annual variations of weather conditions for resulting differences in plant development levels is well-known. The understanding of the relationship of weather to plant and animal growth, known as phenology, has become an important process in annual estimation of crop stages, pest emergence, and disease development. Modern phenology began with recordings of plant and insect development in relation to climate conditions, and over the past fifty years, the development of phenological models has accelerated to provide crop-specific models, and even crop variety-specific models. The models, which are commonly referred as growing degree day (GDD) models, have been developed to understand the timing between accumulated growing degrees and stages of crop development. Combined with pest and disease emergence, which are also phenological processes, the growing degree day models permit producers and crop advisors to make critical decisions on crop protection and enhancement.

Growing degree day models, whether specifically for issues such as insects or diseases planning, or more generally for plant growth, were derived with the understanding that sensible heat derived from atmospheric temperatures drives metabolic processes, affecting the rate of growth and development. In simple terms, a growing degree day is an index of the amount of heat accumulated in a day to drive the metabolic process related to growth or development. Research in the past half-century has led to the establishment of mathematical equations that predict the rate of development at different temperatures for a large selection of crops, and for crop varieties. These mathematical equations are used to predict the rate of insect, disease, or plant development as temperatures fluctuate over time, and provide guidance on upcoming stages of growth and measures to respond to impacts of such growth.

Throughout the duration of a growing season, the speculation of final crop development maturity and the rate of crop development is an important consideration for a grower. From the time of planting and continuing through until the end of a growing season, the uncertainty of how a crop will mature, along with when and with what yield, are considerations of farmers when estimating final cash flows and determining the timing of inputs and actions to support crop development and farm business profitability. Traditional use of crop growth models, such as accumulated growing degree models, utilize accumulated weather conditions that have occurred from crop planting to the current date to provide a historical profile of development. Short-term weather forecasts are also used, but this provides only limited additional insight into crop development for near-term crop management decisions and does not provide a longer-range view of risks and expectations.

Therefore presently-used and known methods in modeling crop growth and development do not provide an adequate estimation of how a crop will develop over a longer range, such as through a remainder of the growing season. The application of climatological data for the crop's geographical region fails to provide anything more than a loose approximation as to development for the remainder of the growing season, since climatological data does not reliably represent a given year's daily conditions.

BRIEF SUMMARY OF THE INVENTION

It is one objective of the present invention a system and method of estimating crop growth and development over an entire growing season using long-range climatological and/or meteorological prediction and forecasting. It is another objective of the present invention to apply a paradigm of long-range weather prediction that is responsive to global weather anomalies, and tuned for anticipated regional weather trends during the entire growing season, to provide a realistic estimation of a crop growth profile from planting date to full crop maturity.

It is another objective of the present invention to augment growing degree day modeling for crop growth development and profiling with long-term weather forecast and prediction, together with routine remotely-sensed crop validation imagery. It is yet another objective of the present invention to provide a system and method of crop development profiling which generates output data that serves as a valuable decision-support tool for projecting future activities in crop management.

The present invention is a system and method of estimating crop growth and development over the course of an entire growing season. The present invention utilizes dynamical extended range weather forecasts spanning the entire duration of the remaining growing season to improve crop growth and development estimation. Using crop growth models, based primarily upon growing degree-days, the present invention generates a profile of crop development until the end of a growing season. The present invention contemplates that in one embodiment, these crop growth models may be executed on a periodic or frequent basis, such as a weekly basis, using an update to the dynamical extended range weather forecasts that consider the ongoing evolution of the region's seasonal weather conditions. Such a generation of a new crop growth and development profile each week may include the growth model output to date using the analyzed and/or observed weather conditions, along with the forecasted weather through the remainder of the growing season. Output from the crop growth and development profile generates a combination of data for use in auxiliary farm management applications. This output may be presented in many ways, such as for example as a graphical display of the crop development attributes as it correlates to observed and predicted weather.

The present invention also utilizes remotely-sensed measurements, such as imagery of crop vitality as depicted from plant spectral analyses, alongside the dynamical extended range weather forecasts. This may be accomplished using techniques such as for example normalized difference vegetation indices (NDVI), which are generated periodically for crop fields supported by growth modeling. Combining spectral analyses of crop vitality with the weather-driven crop growth model results provide a visual reference to the spatial variability across the field of the crop growth model output. As such, remotely-sensed imagery permits extension of crop growth model results beyond the single point represented by the model's execution. This provides both a validation of the crop growth model and serves as a benchmark for evaluation of the forward-looking estimation of crop growth and development using the weekly weather forecast updates of the crop growth model.

Other objects, embodiments, features and advantages of the present invention will become apparent from the following description of the embodiments, taken together with the accompanying drawings, which illustrate, by way of example, the principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

In the following description of the present invention reference is made to the exemplary embodiments illustrating the principles of the present invention and how it is practiced. Other embodiments will be utilized to practice the present invention and structural and functional changes will be made thereto without departing from the scope of the present invention.

Figure 1:
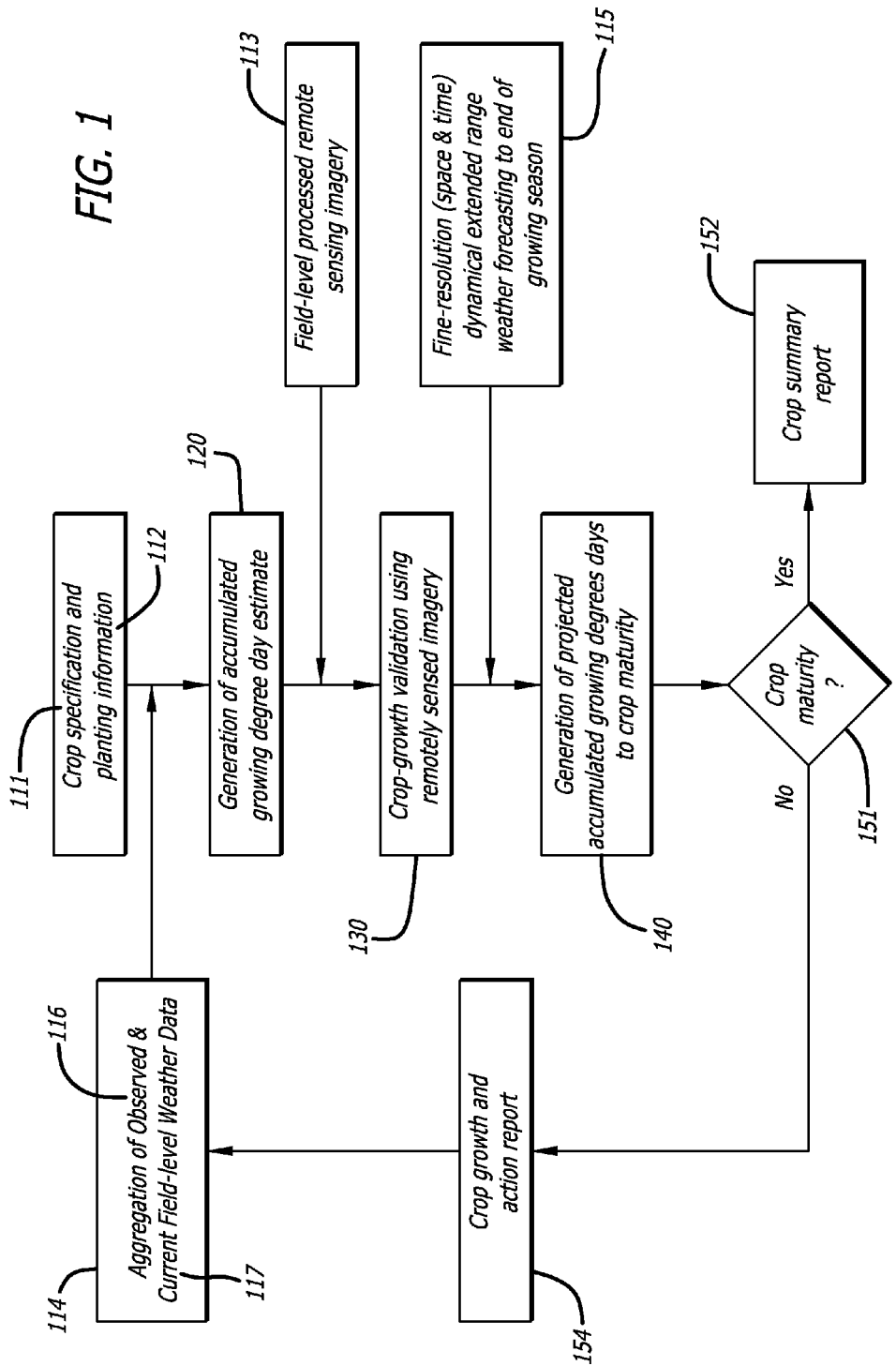
FIG. 1 is a block diagram of data flow within components of an augmented crop growth model according to the present invention.

FIG. 1 is a block diagram of information flow within an augmented crop growth model 100 for projecting crop development throughout an entire growing season. The augmented crop growth model 100 is performed within one or more systems and/or methods that includes several components, including some that are replicated for historical/current and prediction time periods. Each of these components define distinct activities required to support projection of crop maturity from prior to planting at the beginning of a growing season, through to crop maturation and harvesting at the completion of a growing season.

The execution of the augmented crop growth model 100 prior to planting at the beginning of a growing season addresses multiple factors in planning production activities for the year. It addresses a serious challenge, for example, of knowing whether there will be sufficient length to a growing season for a crop to reach its full maturity. Simulating a full growing season before planting provides a projection of the expected timeline of crop growth stages and anticipated date for crop maturity and harvest. This advanced planning increases the likelihood of success during the growing season.

Such advanced planning also has a number of other advantageous uses to the producer or grower. For example, the anticipated date for crop maturity and harvest can be used to determine whether a crop will accumulate sufficient growing degree-days for crop completion. Where this is not expected the producer may make changes to crop selection, change to a shorter season variety of the original crop type, or alter the date of crop planting to permit adequate time for crop maturity to occur. A timeline of crop growth provided prior to planting also gives insight on critical dates for potential pests and disease supporting planning decisions for herbicide and pesticide requirements during the upcoming growing season. This also provides support for anticipating when fertilizer applications are needed or addition of nutrients to finish the crop development.

Figure 2:
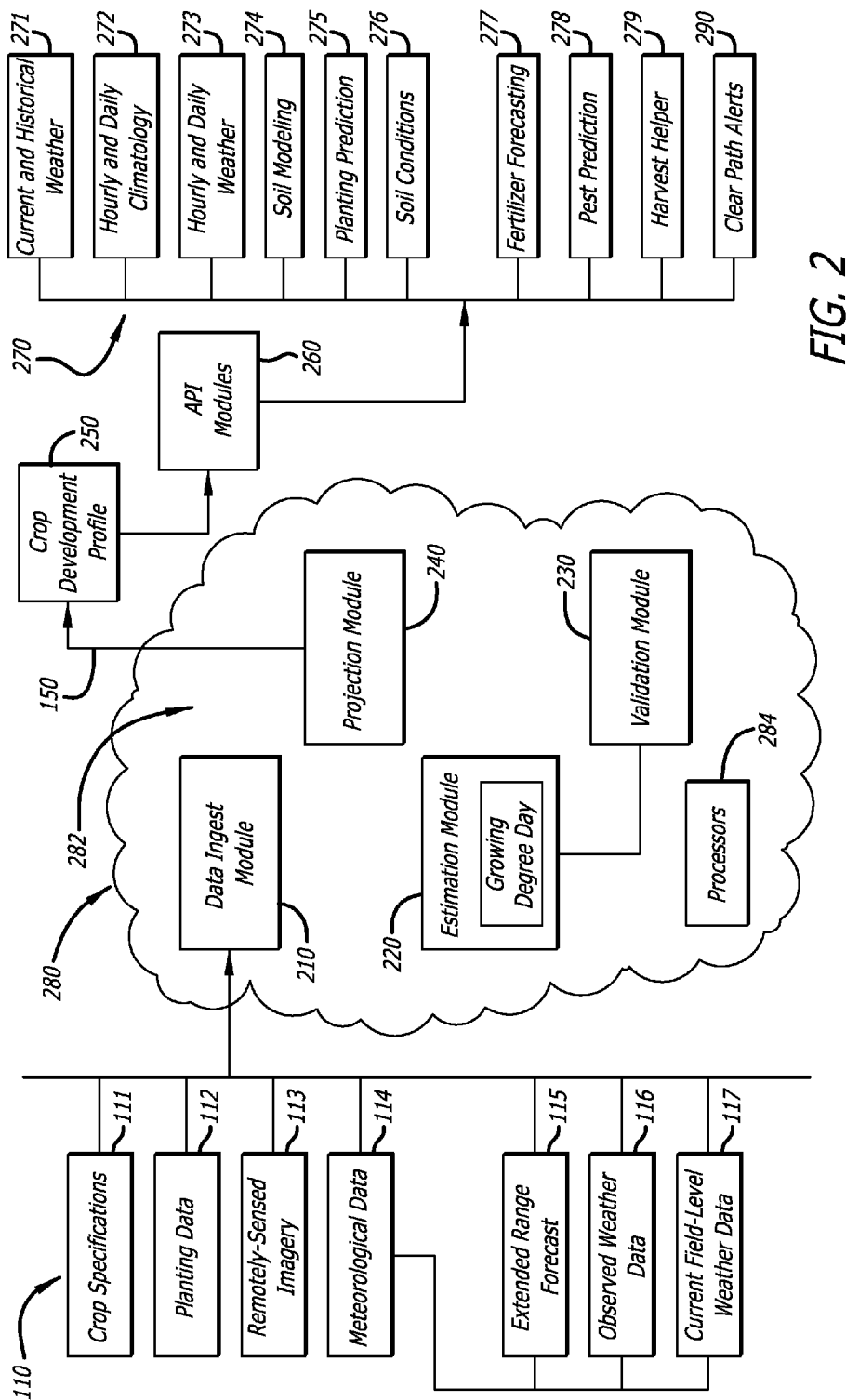
FIG. 2 is systemic diagram of an augmented crop growth model according to the present invention.

The augmented crop growth model 100 ingests input data 110 that includes crop specifications 111 such as for example the type and variety of crop, and other planting data 112, such as for example the date that a field was planted with seed. The input data 110 also includes remotely-sensed imagery data 113, such as for example those captured from orbiting satellites that when processed provide details at a field level resolution. The input data 110 further includes meteorological data 114, which includes both dynamical extended range weather forecast information 115 through to the completion of a growing season, as well as observed weather data 116 that has occurred during the current growing season and current field-level weather data 117. All of this input data is ingested into the augmented crop growth model 100 via a data ingest module 210 as shown in the system diagram of FIG. 2.

The augmented crop growth model 100 ingests these inputs to generate a crop development profile 250, such as for example in a growing degree day model, by describing the heat accumulated to support growth and development. This is used to generate instances of an accumulated growing degree day estimate 120 in an estimation module 220 for time periods throughout a growing season, such as daily or weekly. The augmented crop growth model 100 also ingests field-level remotely-sensed image data 113, and performs a crop growth validation 140 using such imagery in a validation module 230. The augmented crop growth model may also ingest, as noted above, meteorological information 114 in the form of dynamical extended range weather forecast data 115, which is used to perform additional instances of generating an accumulated growing degree day estimates 120 in the estimation module 220 to continue building the crop development profile 250. The augmented crop growth model 100 then performs a projection of accumulated growing degree days to crop maturity 130 in a projection module 240, which contributes to a progression of the crop development profile 240 to the end of the growing season.

The crop development profile 250 is therefore output data 150 of the augmented crop growth model 100. Once the augmented crop growth model 100 has completed this projection phase 140, the present invention determines whether a crop has reached maturity 151. This determines a form of one type of output data 150. Where a crop has reached maturity at step 151, the model 100 generates crop summary reports 152. If crop maturity has not been reached at step 151 (and therefore the growing season is still underway), the model 100 generates crop growth and action reports 154. Output data 150 may further be used for generation of advisory services 270 in one or more application programming interface (API) modules 260 as described in more detail herein.

System components of the augmented crop growth model 100 include one or more data processing modules 282 within a computing environment 280 that also includes one or more processors 284 and a plurality of software and hardware components. The one or more processors 284 and plurality of software and hardware components are configured to execute program instructions to perform the functions of the augmented crop growth model 100 described herein, and embodied in the one or more data processing modules 282.

The crop specifications 111 and the planting data 112 provide various aspects of the crop information that form a basis for the configuration of the phenological processes analyzed in the augmented crop growth model 100 of the present invention. The crop specifications 111 provide two general categories of information, which are the type of crop to be planted, and the variety, or cultivar, of that crop type. For example, a crop type could be corn and the variety of corn could be standard, sugary enhanced, or super-sweet. The type of crop determines a set of generally defined growth characteristics of the crop, such as occurrence of various leave stages and produce development stages for the crop type. Specifying the variety fine-tunes these growth characteristics to specify the timing to each stage, nutrient requirements per stage, pest/disease susceptibility per stage, and the temperature thresholds for grow/no growth of the crop. These variety characteristics are established as a particular crop variety is genetically developed by researchers and are often associated with a particular seed product name. Crop specifications 111 may further include crop practices, such as whether the crop is organic, genetically modified, non-genetically modified, irrigated, and non-irrigated. Together, the type of crop and its variety informs the generation of the crop development profile 250 for the crop and establishes a basis for analyzing related factors such as pests and diseases. This information on pests and disease provides information on required weather conditions that lead to the emergence of pests and disease and includes information on eradication measures should they occur. The presence of factors such as these is important at particular times during specific growth stages and throughout the growth cycle, and becomes a significant part of notification processes within one or more advisory services 270 within the present invention.

Other crop specifications 111, such as the precise location of crop field, provide a basis for determining weather conditions during the growing season. These locations can be expressed either in positional coordinates such as latitude and longitude, and may also be expressed in terms of platting data representing boundaries and location within a township, area, range, or section. Regardless, the present invention may incorporate appropriate algorithms to extract data such as the positional coordinates and platting data.

Planting information 112 such as the planting date may be provided as either an anticipated date or an actual date. The anticipated planting date may be used, for example, where activity is being modeled in the augmented crop growth model 100 prior to the growing season. Otherwise, the actual date of planting is used. It should be noted in the case of modeling for pre-growing season activity that the augmented crop growth model 100 may be reset when the crop is planted and the actual planting date becomes known. Other planting information 112 includes soil information such as the soil type, current and/or forecasted soil conditions, overall soil profile, levels of vegetative debris existing at the time of planting, nutrient levels present at planting, and the soil moisture history since the previous crop. Still other planting information 112 may include plant depth, plant population, and row width. Planting information becomes a significant part of notification processes within one or more advisory services 270 within the present invention Meteorological data 114 is collected for the specified geographical area which a crop is located, using either temperature sensors in the crop field or from fine-resolution analyses of weather derived from sensors across a region that includes the crop field, or both (since the presence of temperature sensors within crop fields for all possible instantiations of the augmented crop growth model 100 may not be feasible). For the purpose of the phenological processes modeled in the present invention, these temperature sensors may be configured to continuously monitor maximum and minimum temperatures over 24-hour periods. The spatial analysis of observed, sensible air temperatures may employ a Barnes objective analytical scheme that permits exponential weighting functions to maximize the information of closer observations to the location of interest. This interpolation is a multi-pass method given by the equation:

$$g(x_i, y_j) = g_0(x_i, y_j) + \sum (f(x, y) - g_0(x, y)) \exp\left(-\gamma \kappa \frac{\pi^2}{\lambda}\right) \tag{1}$$

where $g_0(x_i, y_j)$ is the initial estimated value at a grid location as given by the equation:

$$g_0(x_i, y_j) = \frac{\sum_k w_{ij} f_k(x, y)}{\sum_k w_{ij}}. \tag{2}$$

The value of $\gamma$ controls the smoothing of data, while $\lambda$ is an expression of the minimum wavelength of disturbances resolved in the analysis. The weighting function, w, is specified at each m data points as an exponentially decreasing function of the distance, r, away from the grid point by the equation:

$$w_{ij} = \exp\left(-\frac{r_m^2}{\kappa}\right) \tag{3}$$

where $\kappa$ controls the width of the Gaussian function. However, once the maximum and minimum temperatures are obtained either from in-situ sensors or from spatially analyzed observations, data are stored in the application database for routine use by augmented crop growth model 100.

The canonical form of the growing degree day calculation is expressed as:

$$GDD = \left[\frac{(T_{Max} + T_{Min})}{2}\right] - T_{Base} \tag{4}$$

where $T_{max}$ is the daily maximum sensible air temperature, $T_{min}$ is the daily minimum sensible air temperature, and $T_{Base}$ is the sensible air temperature where growth process do not occur. The value for $T_{Base}$ varies by crop type and even by cultivars of a crop type. Measurement or analysis of daily maximum and minimum sensible air temperatures is used to describe the heat accumulated to support growth and development. As such the value of a growing degree day is to refer not to actual days but rather a representation of heat accumulation for a day that can be used to estimate the phyllochron of plant growth and eventual plant maturity.

Using a climatological average temperature for a given location, the accumulated growing degree day at that location can be used to express the thirty-year average for the number of days elapsed since planting. Most crops exhibit a physiological growth limit when exposed to large amounts of heat. Thus, Eq. 1 above is often modified to place limits on growing degree day accumulation during periods where temperatures exceed an upper threshold value. The same is true where either $T_{Max}$ or $T_{Min}$ fall below the base temperature threshold for plant growth. The present invention may use the diurnal maximum and minimum single values of sensible air temperature gathered either by direct field observations, by spatial analysis of surrounding observed sensible air temperatures, or through prediction of daily maximum and minimum sensible air temperature from numerical weather prediction models described below. Other methods of determining daily average sensible air temperatures may also be utilized, such as summing all hourly values to derive a twenty-four hour average.

Regardless of the method used, multiple instances of the accumulated growing degree day estimation are contemplated by the present invention. Initial and ongoing instances involve the use of historical and current sensible air temperatures gathered and/or analyzed since crop planting. This may be represented by the observed weather data 116 that has occurred during the current growing season and the currently-experienced field-level weather data 117. The resulting accumulated growing degree day estimate 120 represents the phenological activity of the crop designated during the initial and ongoing phases of the augmented crop growth model 100. An initial growing degree day calculation for the crop serves as the first marker on the crop development profile 250 along the path to the crop maturity date. Each subsequent calendar day (or other time interval as specified by a user of the present invention) provides an additional marker on the crop development profile 250 and serves as a reference point for assessing factors such as potential insect and disease hazards in the short-term growth the crop.

The use of field-level processed remotely-sensed imagery 113 provides additional support for an assessment of current crop state and growth stage in the crop-growth validation phase 130 of the augmented crop growth model 100. One source of image data representing this remotely-sensed imagery 113 is satellite systems, such as fine temporal resolution low-earth orbit satellites that provide a minimum of three spectral bands. Other sources are also contemplated, such as for example unmanned aerial systems, manned aerial reconnaissance, lower temporal frequency earth resources satellite such as LANDSAT and MODIS, ground-based robots, and sensors mounted on field and farm equipment. Regardless of the source, this imagery 113 is field-navigated to provide users with the most recent high-resolution depiction of the crop field. Imagery 113 in the form of image data may be delivered on a web or application-based tool configured within the augmented crop growth model 100, and additional tools may be provided for spatially navigating the image data and overlaying a variety of weather data elements.

The field-level remotely-sensed imagery 113 is used to map the crop field and generate a time-series profile 250 of crop development and vitality. Both direct provision of field-level processed remotely-sensed imagery 113 and imagery 113 that has been analyzed may be provided. Imagery 113 is analyzed using a normalized difference vegetative index (NDVI) that provides the user with an evaluation of plant health, biomass and nutrient content. Other approaches may also be employed for such analysis, such as: Modified Chlorophyll Absorption Ratio Index/Optimized Soil-Adjusted Vegetation Index (OSAVI), Triangular Chlorophyll Index/OSAVI, Moderate Resolution Imaging Spectrometer Terrestrial Chlorophyll Index/Improved Soil-Adjusted Vegetation Index (MSAVI), and Red-Edge Model/MSAVI. Regardless, analysis of imagery 113 provides a meaningful further input to the augmented crop growth model 100 because plants absorb short-wave radiation from the sun between wavelengths of 400-nm and 750-nm, which is their photo-synthetically active spectral region. Thus, healthy plants appear darker at these wavelengths. The addition of leaves on healthy plants results in strong reflection in the near infrared spectrum. These features provide the basis for categorizing plant species as well as monitoring vitality of plants using the NDVI analysis. The NDVI relationship is given for the red and green spectral bands in this application as $$NDVI_{red} = \frac{\left[\frac{NIR_{ref}}{NIR_{inc}} - \frac{Red_{ref}}{Red_{inc}}\right]}{\left[\frac{NIR_{ref}}{NIR_{inc}} + \frac{Red_{ref}}{Red_{inc}}\right]} \quad (5a)$$

$$NDVI_{green} = \frac{\left[\frac{NIR_{ref}}{NIR_{inc}} - \frac{Green_{ref}}{Green_{inc}}\right]}{\left[\frac{NIR_{ref}}{NIR_{inc}} + \frac{Green_{ref}}{Green_{inc}}\right]} \quad (5b)$$

where $NIR_{ref}$, $Red_{ref}$ and $Green_{ref}$ denote magnitudes of reflected light in the near infrared, red and green bands and $NIR_{inc}$, $Red_{inc}$, and $Green_{inc}$ denote magnitudes of incident in the same three bands as the reflected.

Routine ingest of the remotely-sensed imagery 113 for the crop field provides the time-series data needed to denote change in the crop, and is correlated with the crop growth stage estimated by the amount of accumulated growing degree days. This enables a comparison that allows growers to calibrate the accumulated growing degree day estimates 120 to ensure that appropriate decisions are made in relation to the crop growth actions suggested by the output data 150, particularly in the crop summary report 154 discussed further herein.

In one embodiment of the present invention, the validation module 230 may be configured to generate notifications to users of the augmented crop growth model 100 when a validation 130 identifies a change in a crop's growth. Such notifications ensure that appropriate decisions are made in relation to the crop growth actions, and they may be provided to users at times and to devices at the direction of the user. For example, when the validation phase 130 of the augmented crop growth model 100 generates a change in crop growth, a tactile notification may be provided to the user's mobile device, such as in a haptic vibration. Mobile devices may include any device capable of being used to view or manipulate data generated by the present invention, whether it be a desktop, laptop, tablet, or notebook computer, or another mobile device such as data-enabled telephone.

Further instances of the accumulated growing degree day estimation 120 occur sequentially with, and following, prior/initial instances to perform the projection 140 of accumulated growing degree days to crop maturity. These latter instances apply a dynamical extended range weather forecast 115 to provide daily maximum and minimum temperatures for the crop location for a period extending to the crop maturity date projected by the accumulated growing degree day estimation 120. In a manner similar to the daily accumulation of field-level sensible air temperatures, gridded dynamical extended range weather forecasts 115 of sensible air temperature are used to determine the predicted values using the crop field's latitude and longitude. Daily projection 140 of accumulated growing degree day estimation 120 are made for each subsequent date beyond the current crop date and until the total accumulated growing degree day estimation 120 exceeds the crop maturity value specified for the crop at issue. Each day serves as a marker on the crop development profile 250 in a manner similar to the accumulated growing degree days using observed/analyzed sensible air temperatures from the first instance of the crop growth model run. Thus, the combined instances of the accumulated growing degree day estimations 120 provide an entire season of daily growing degree days for use in crop growth interpretation.

As noted above, the use of phenological crop growth models, such as growing degree day models, to provide future expectations on growth have previously been limited by the scope of predicted weather information included for estimating future growing degree days. Use of climatological normal values assumes that the current year will be equivalent to the average of the previous climate period that spanned thirty years. Unfortunately, the likelihood of matching this thirty-year average condition, particularly summed over an entire growing season, is very low and unrealistic. The present invention modifies this climatological average to account for annual and seasonal variations to enable a more realistic profile for projection of sensible air temperatures (and also precipitation) for an entire growing season.

The augmented crop growth model 100 applies known methods for inter-seasonal to inter-annual climate prediction, which have evolved into a combination of deterministic and statistical modeling schemes that permit the capture of long-term low-frequency features. Such modeling schemes are known as dynamical extend range weather forecast models. Dynamical extended range weather forecasting is one of the most complex and challenging forecasting problems as it requires global analyses for the specification of observed initial and boundary conditions, the use of sophisticated numerical weather prediction models, a statistical treatment of the model results, and a verification of the forecast results as a feedback into forecast refinement.

The use of dynamical extend range weather forecasting in the augmented crop growth model 100 of the present invention involves accounting for the future low frequency variability within the atmosphere to modify the climatological expectations during the span of the growing season. In one embodiment of the present invention, the modeling process involves the use of two data assimilation systems and two forecasting systems. The two data assimilation systems are used to provide historic and current atmospheric and land surface initial conditions and also global ocean temperatures. The two forecast systems incorporate the U.S. National Centers for Environmental Predictions (NCEP) Global Forecast System (GFS) for atmospheric predictions and the Geophysical Fluid Dynamics Laboratory Modular Ocean Model to provide sea-surface temperature predictions. To provide computational efficiencies the GFS is run at a horizontal grid resolution of approximately 100-kilometers using a spectral triangular truncation of 126 waves. To maintain consistency between the data assimilation and atmospheric forecasting systems, the same horizontal grid resolution is used for each. Software and data supporting the above are publicly available from the NCEP.

In the present invention, the dynamical extend range weather forecast models are executed daily to provide a complete global dataset for use in initializing the subsequent model run, and to be used to supply localized values for the growing degree day projections for individual crop locations. Given the 100-kilometer grid spacing of the dynamical extend range forecast (DERF) models, the data is downscaled to map predicted values to each crop field location. This downscaling is accomplished with a linear regression using the predicted values along with both observed conditions and error-corrected previous forecasts for the desired location.

It should be noted that in the present invention, additional sources of meteorological data 114 may be utilized to provide one or more of the observed weather data 116 that has occurred during the current growing season, the current field-level weather data 117, and the dynamical extended range weather forecasts 115, for example as data that is complementary to the two data assimilation systems and two forecasting systems noted above. Such additional sources of weather data may include data from both in-situ and remotely-sensed observation platforms. For example, numerical weather models (NWP) and/or surface networks may be combined with data from weather radars and satellites to reconstruct the current weather conditions on any particular area to be analyzed. There are numerous industry NWP models available, and any such models may be used as sources of meteorological data 114 in the present invention. Examples of NWP models at least include RUC (Rapid Update Cycle), WRF (Weather Research and Forecasting Model), GFS (Global Forecast System) (as noted above), and GEM (Global Environmental Model). Meteorological data 114 is received in real-time, and may come from several different NWP sources, such as from Meteorological Services of Canada's (MSC) Canadian Meteorological Centre (CMC), as well as the National Oceanic and Atmospheric Administration's (NOAA) Environmental Modeling Center (EMC), and many others. Additionally, internally or privately-generated "mesoscale" NWP models developed from data collected from real-time feeds to global observation resources may also be utilized. Such mesoscale numerical weather prediction models may be specialized in forecasting weather with more local detail than the models operated at government centers, and therefore contain smaller-scale data collections than other NWP models used. These mesoscale models are very useful in characterizing how weather conditions may vary over small distances and over small increments of time. The present invention may be configured to ingest data from all types of NWP models, regardless of whether publicly, privately, or internally provided or developed.

Other sources of data ingested into the augmented crop growth model 100 may include image-based data from systems such as video cameras, and data generated from one or more vehicle-based sensing systems, including those systems coupled to computing systems configured on farm equipment, or those systems configured to gather weather data from mobile devices present within vehicles, such as the mobile telephony devices and tablet computers as noted above. Crowd-sourced observational data may also be provided from farmers using mobile telephony devices or tablet computers using software tools such as mobile applications, and from other sources such as social media feeds. Meteorologist input may be still a further source of data.

The integration of crop growth status with projected sensible air temperatures for the remainder of the growing season provide the grower or crop consultant a valuable decision-support tool for projecting future activities in crop management. Before the commencement of the growing season such estimations for the growing season identify variations in the thirty-year average climate for the upcoming growing season that can lead to refined determination of crop selection, seed variety and planting decisions. After planting, this information provides guidance on fertilizer management, irrigation, and application of herbicide and pesticide during the growing season.

Periodic crop growth action reports, provided at user-defined intervals such as daily, weekly, or bi-weekly, present the user with three primary categories of information. First, it provides an updated development profile of accumulated growing degree days since planting and identifies the transition of plant stages that have occurred and that are presently occurring. Next, it provides a validation of the plant growth stages using remotely sensed imagery that includes a full NDVI analysis of the crop field. Combined, these two parts provide a short-term roadmap on actions needed in crop management. The third part provides a detailed, daily accounting of future accumulated growing degree day up to crop maturity. This latter includes future physiological stages and their timing. It also provides a summary of remaining threats to the crop including pests, potential diseases, and threats of drought and excessive moisture. The time to maturity includes a specification of a calendar date when crop maturity is expected, and for harvest timing.

At the end of the crop growing season and with the last of the routinely generated crop growth action reports, a crop summary report is generated. This summary report provides an accumulation of crop growth prediction statistics along with a validation summary. This summary report provides growers with a snapshot of the growing season indicating how the growing season progress compared to the long-term average expectations for a growing season of the specific crop planted at that location.

The present invention also contemplates that output data 150 may be generated for visual representation of the information contained, for example on a graphical user interface. For example, users may be able to configure settings for, and view various aspects of, the augmented crop growth model 100 using a display on such a graphical user interfaces, and/or via web-based or application-based modules. Tools and pull-down menus on such a display (or in web-based or application-based modules) may also be provided to customize the estimation 120, validation 130, and projection 140 phases of the model 100, as well as the output data 150. Examples of this include the tactile notifications of changes in crop growth discussed above. Other types of notifications may include those provided via applications resident on mobile telephony, tablet, or wearable devices are also possible, such as for example a voice-based output generated to verbally notify farmers of possible disease or pest risk.

As noted above, the output data 150 of the augmented crop growth model 100 may be used to generate a plurality of advisory services 270 in one or more application programming interface (API) modules 260. These advisory services 270 provide enhanced decision-making support to precision agricultural production within the present invention.

These advisory services 270 are driven by the generation of the crop development profile 250 that results in the crop growth and action reporting and crop summary reporting aspects of the output data 150. Each of these advisory services 270 enriches the utilization and application of the augmented crop growth model 100.

One such advisory service 270 is a current and historical weather reporting service 271. Site-specific weather information is an important element of field recordkeeping in agricultural production. Using the field position information provided for the accumulated growing degree day calculations, current and historical weather for the field location may be provided as an advisory service for specific geographical locations. Accordingly, this information has a dual utility in the present invention, as it is also utilized as a routine input data (observed weather data 116 and current field-level weather data 117) to the accumulated growing degree day estimation 120 to provide the needed maximum and minimum temperatures for computing actual growing degree days. The present invention therefore contemplates using this information as both as input to the augmented crop growth model 100 and, together with geo-positional information, as a form of output data 150 as an advisory service 270.

Another advisory service 270 is an hourly and daily climatology reporting service 272. Although the output data 150 is generally related to dynamical computation of growing degree days for a specific field and crop type, users of the present invention are capable of contrasting the dynamical growing degree days with expected growing degree days relative to the thirty-year climatology. This enables one to contrast the difference experienced in a given year relative to the long-term average derived from climatology data provided on an hourly or daily basis. Accordingly, hour-by-hour and daily climatological averages for specified location(s) and time period(s) can be provided as a reporting service 272. In addition, this reporting service 272 provides a probability distribution of various weather-related metrics including the number of remaining growing degrees based upon climatology.

Another advisory service 270 is an hourly and daily weather forecasting service 273. The use of routine weather forecast information is a staple of agricultural production support operations and planning, and this advisory service 270 provides such weather forecast information to augment the routine generation and reporting of accumulated growing degree days. Accordingly, the present invention can be configured to generate a weather forecast in conjunction with the accumulated growing degrees day estimation 120 in the output data 150. The weather forecast service 273 is available in multiple data formats ranging from text, site-specific graphics or as a map-based display on a graphical user interface.

A soil modeling service 274 is another advisory service 270 contemplated within the scope of the present invention. One API module 260 applies the crop development profile 250 and output data 150 to a sophisticated soil model to generate information that provides a better understanding of current and future soil conditions relative to historical soil conditions. Such a soil model support the use of existing soil properties e.g., organic matter, soil type, etc., tillage practices, presence of tile drainage, and irrigation history, along with the advanced long-range weather forecasting. This coupling of modeled soil characteristics with advanced weather forecasting information from the dynamical extended range forecast 115 for an entire growing season provides a valuable tool for indicating crop potential. The output of an API module generating this soil modeling service 274 may be further configured to provide a detailed past-through-future analysis of soil temperature and moisture assessments, including freeze and thaw information, the amount of water 'throughput', runoff or ponding of soils, and an important interpretation of workability of the soils. Soil models contemplated for use in the present invention may include models such as the EPIC, APEX, and ICBM soil models.

A planting prediction reporting service 275 may also be provided as an advisory service 270. When utilized prior to the growing season using the season-long dynamic extended range weather forecasting capabilities, the augmented crop growth model 100 of the present invention can be configured to simulate an entire growing season before it occurs. Applying this to assess the timeline of accumulated growing degree days throughout the growing season when planted at differing times is an inherent benefit to optimizing successful completion of a selected crop and/or making an informed decision as to what type of crop or its cultivar to select. When coupled with an entire growing season's growing degreed days estimation 120 and the weather output from the dynamical extended range weather forecast 115, a planting prediction reporting service 275 provides multi-faceted information regarding planting operations, such as near-term field conditions (soil moisture and temperature) and expected seasonal growth metrics. This planting prediction reporting service 275 provides likely periods of suitability of weather and soil conditions, including soil workability, soil temperatures, potential adverse post-planting weather conditions, and the likelihood that the crop will reach maturity. The planting prediction reporting service 275 may also utilize the output data 150 in the hourly and daily climatology reporting service 271 to provide a further comparison of the dynamical extended range weather forecast-driven growing degree days planting predictions to one based upon climatology.

Another advisory service 270 is soil conditions forecasting service 276. The soil modeling service 274 can be used with predicted weather to provide an estimate of future soil conditions in this advisory service 270. Using the dynamical extended range forecast data 115, a forecast of soil temperature and moisture conditions for the specified field location can generated. Such a forecast in this service 275 enables anticipation of periods of suitable soil conditions for field operations, including workability, particularly those after periods of rainfall.

Yet another advisory service 270 as an output of the augmented crop growth model 100 is a fertilizer forecasting service 277. Knowledge of expected growing degree days provides a timeline for the various stages of crop growth, and each of these stages has differing nutrient needs. The fertilizer forecasting service 277 uses timing of these stages predicted by the accumulated growing degree day timeline along with the soil modeling data from the soil modeling service 274 to identify periods of suitability of soil conditions for continued satisfactory crop growth, and anticipates the impact of soil saturation on the loss of available nutrients via leaching, denitrification, and other soil and water related crop growth factors. The fertilizer forecasting service 277 may also provide a recommendation of how much fertilizer should be applied and an estimate of how much of the fertilizer applied at the crop's location may be leached away by excessive moisture and soil saturation. The fertilizer forecasting service 277 may also be used retrospectively to evaluate fertilizer effectiveness loss due to soil and rain conditions that have recently occurred.

Another advisory service 270 as an output of the augmented crop growth model 100 is a pest prediction service 278. The presence of pests has differing impacts depending upon the stage of a crop. Similarly, the variability of the weather can give rise to potential crop disease conditions that also have differing impacts depending upon crop stage. The timeline identification of the various crop stages in the accumulated growing degree day estimation 120 is a valuable tool for deciding the best course for integrated pest management activities. This information, when incorporated in the pest prediction service 278, provides assessments of the conduciveness of weather conditions to various disease and pest pressures at the current time through the end of the growing season. The pest prediction information from this advisory service 270 helps in assessing the relative risk vs. reward i.e., cost vs. benefit, of potential pesticide applications to prevent crop damage due to factors such as disease or insects.

Another advisory service 270 as an output of the augmented crop growth model 100 is a "harvest helper" reporting service 279. The routinely-updated accumulated growing degree day estimation 120 of the present invention provides an important metric for determining when a crop will reach maturity. However, it should be noted that the harvest of a crop involves factors such as appropriate weather conditions at the time of maturity to permit a successful harvest. The harvest helper reporting service 279 estimates the timing of harvest operations, and weighing the relative costs of fuel-based forced-air drying vs. the risks associated with loss of standing crop to adverse weather conditions. The harvest helper reporting service 279 also provides information on possible loss of field workability due to the formation of frost in the soils prior to post-harvest tillage. This reporting service 279 may be further used to develop tools that include estimating standing crop dry-down rates, anticipated harvest dates and suitability, fuel consumption optimizers for forced-air drying, and indicators of plant 'toughness' for anticipating harvest windows.

Another advisory service 270 as an output 150 of the augmented crop growth model 100 is a "ClearPathAlerts" service 280. The importance of information provided to production agriculture in the present invention dictates a necessity for an effective and direct method of conveying information. The ClearPathAlerts service 280 may utilize a 'push' technology for immediate and direct dissemination of information provided as output data 150 from the augmented crop growth model 100. The API module 260 that generates this service 280 may be configured to so that users may receive alerts of important combinations of weather conditions, risk factors, and decision-support aides for the purposes of managing and timing field operations. This is supported by user-specified elements including alert parameters, location(s), lead time(s), time(s) of day, and the particular device(s) to receive the alerts.

The systems and methods of the present invention may be implemented in many different computing environments 280. For example, they may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, and any comparable means. In general, any means of implementing the methodology illustrated herein can be used to implement the various aspects of the present invention. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors), memory, nonvolatile storage, input devices, and output devices. Furthermore, alternative software implementations including, but not limited to, distributed processing, parallel processing, or virtual machine processing can also be configured to perform the methods described herein.

The systems and methods of the present invention may also be partially implemented in software that can be stored on a storage medium, executed on programmed general-purpose computer with the cooperation of a controller and memory, a special purpose computer, a microprocessor, or the like. In these instances, the systems and methods of this invention can be implemented as a program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, artificial intelligence, fuzzy logic, expert system or combination of hardware and software that is capable of performing the data processing functionality described herein.

It is to be understood that other embodiments will be utilized and structural and functional changes will be made without departing from the scope of the present invention. The foregoing descriptions of embodiments of the present invention have been presented for the purposes of illustration and description. It is not intended to be exhaustive or to limit the invention to the precise forms disclosed. Accordingly, many modifications and variations are possible in light of the above teachings. It is therefore intended that the scope of the invention be limited not by this detailed description.

The invention claimed is:

1. A computerized method comprising:
inputting a plurality of data that includes crop-specific information, planting specifications, remotely-sensed imagery, and meteorological data that includes fine-resolution dynamical extended range weather forecast information, the fine-resolution dynamical extended range weather forecast information representing a time period extending through to a crop maturity date;
modeling the input data in a plurality of data processing modules within a computing environment in which the plurality of data processing modules are executed in conjunction with, and performed on, at least one computer processor, the data processing modules configured to generate a profile of crop development to a maturity stage by performing, over the course of a growing season, a crop growth model that includes the steps of 1) generating an accumulated growing degree days estimate of crop growth stages, 2) validating the estimate of crop growth stages by comparing the estimate with a time-series profile of crop growth data derived from the remotely-sensed imagery of a crop field, 3) determining actual growth stages from direct user-provided field observations representing at least one of temperature values and crop growth, at least one time during a crop growing season, 4) identifying differences between the estimate of crop growth stages and crop growth changes indicated by the comparison with remotely-sensed imagery and from the actual growth stages, and adjusting the estimate, and 5) generating an accumulated growing degree days projection of the crop growth stages by extracting daily maximum and minimum air temperatures from forecasted information based on the dynamical extended range weather forecast information to describe heat accumulated for a crop location for the time period extending through to the crop maturity date; and
generating one or more of a crop growth action report and a crop summary report from the profile of crop development.

2. The method of claim 1, wherein the crop-specific information includes a crop type and a variety of crop type that determines a set of growth characteristics of the crop that enables the data processing modules to generate the profile of crop development, the set of growth characteristics including a timing to growth of each crop growth stage, nutrient requirements per crop growth stage, pest and disease susceptibility per crop growth stage, and one or more temperature thresholds for crop growth conditions.

3. The method of claim 1, wherein the generating an accumulated growing degree days estimate of a crop's growth stage repetitively occurs over a course of a growing season in a plurality of instances of generating a profile of crop development.

4. The method of claim 3, wherein the meteorological data further includes observed weather data for a geographical area including the crop field, and current field-level weather data for the geographical area including the crop field, the observed weather data and the current field-level weather data being repetitively applied to the crop growth model during the time period where the crop maturity date has not yet been reached.

5. The method of claim 4, wherein the generating an accumulated growing degree days estimate of crop growth stages generates an accumulated growing degree day estimate on a daily basis until a total accumulated growing degree day estimate exceeds the time period extending through to the crop maturity date.

6. The method of claim 1, wherein the crop summary report is generated where the crop has reached maturity, and the crop growth and action report is generated where the crop has not yet reached maturity.

7. The method of claim 1, further comprising generating a notification to a user when a validation of an estimate of crop growth stages identifies a change in the crop's growth stage, wherein the notification is provided to the user as a tactile indication on a mobile device.

8. The method of claim 1, further comprising analyzing the remotely-sensed imagery using a normalized difference vegetative index to evaluate at least one of plant health, biomass, and nutrient content.

9. The method of claim 1, further comprising providing the one or more of a crop growth action report and a crop summary report to one or more application protocol interface modules each configured to generate an advisory service for agriculture management applications.

10. The method of claim 1, wherein the crop growth model is performed prior to a beginning of a growing season, to simulate a full growing season to project an expected timeline of crop growth stages and an anticipated crop maturity date.

11. A system comprising:
a computer processor; and
at least one non-transitory computer-readable storage medium operably coupled to the computer processor and having program instructions stored therein, the computer processor being operable to execute the program instructions to generate a profile of crop development to a maturity stage by performing, over the course of a growing season, a crop growth model within a plurality of data processing modules, the plurality of data processing modules including:
a data ingest module configured to input crop-specific information and planting specifications, remotely-sensed imagery, and meteorological data that includes fine-resolution dynamical extended range weather forecast information, the fine-resolution dynamical extended range weather forecast information representing a time period extending through to a crop maturity date;
an estimation module configured to generate an accumulated growing degree days estimate of crop growth stages;
a crop validation module configured to 1) compare the estimate with a time-series profile of crop growth data derived from remotely-sensed imagery of a crop field to validate the estimate of crop growth stages, 2) determine actual growth stages from direct user-provided field observations representing at least one of temperature values and crop growth, at least one time during a crop growing season, and 3) identify differences between the estimate of crop growth stages and crop growth changes indicated by the comparison with remotely-sensed imagery and from the actual growth stages, and adjusting the estimate;

a projection module configure to generate an accumulated growing degree days projection of the crop growth stages by extracting daily maximum and minimum air temperatures from forecasted information based on the dynamical extended range weather forecast information to describe heat accumulated for a crop location for the time period extending through to the crop maturity date; and a crop growth reporting module configured to generate one or more of a crop growth action report and a crop summary report from the profile of crop development.

12. The system of claim 11, wherein the crop-specific information includes a crop type and a variety of crop type that determines a set of growth characteristics of the crop that enables the data processing modules to generate the profile of crop development, the set of growth characteristics including a timing to growth of each crop growth stage, nutrient requirements per crop growth stage, pest and disease susceptibility per crop growth stage, and one or more temperature thresholds for crop growth conditions.

13. The system of claim 11, wherein the estimation module generates an accumulated growing degree days estimate of crop growth stages repetitively over a course of a growing season, in a plurality of instances of generating a profile of crop development.

14. The system of claim 11, wherein the meteorological data further includes observed weather data for a geographical area including the crop field, and current field-level weather data for the geographical area including the crop field.

15. The system of claim 11, wherein the estimation module generates an accumulated growing degree day estimate on a daily basis until a total accumulated growing degree day estimate exceeds the time period extending through to the crop maturity date.

16. The system of claim 11, wherein the crop growth reporting module generates the crop summary report where the crop has reached maturity, and generates the crop growth and action report where the crop has not yet reached maturity.

17. The system of claim 11, wherein the crop validation module generates a notification to a user when a validation of crop growth identifies a change in the crop's growth, wherein the notification is provided to the user as a tactile indication on a mobile device.

18. The system of claim 11, wherein the crop growth model analyzes the remotely-sensed imagery using a normalized difference vegetative index to evaluate at least one of plant health, biomass, and nutrient content.

19. The system of claim 11, further comprising an application programming interface module configured to receive the profile of crop development and generate one or more advisory services for agriculture management applications.

20. A method projecting crop growth over the course of a growing season, comprising:

within a computing environment comprised of a computer processor and at least one non-transitory computer-readable storage medium operably coupled to the computer processor and having program instructions stored therein, the computer processor being operable to execute the program instructions to augment a crop growth model configured to perform the steps of:

estimating an accumulated growing degree days of a plurality of crop growth stages, by generating a profile of crop development over the course of a crop growing season through to a maturity stage;

validating the estimate of crop growth stages by comparing the estimate with a time-series profile of crop growth data derived from remotely-sensed imagery of a crop field;

adjusting the estimate based on differences between the estimate of crop growth stages and crop growth changes indicated by the comparison with remotely-sensed imagery and from actual growth stages determined from direct user-provided field observations; and projecting accumulated growing degree days of the crop growth stages for a time period extending through to the crop maturity date by extracting daily maximum and minimum air temperatures from forecasted information based on dynamical extended range weather forecast information to describe heat accumulated for a crop location.

21. The method of claim 20, wherein the estimating an accumulated growing degree days of a plurality of crop growth stages repetitively occurs over a course of a growing season, in a plurality of instances of generating a profile of crop development.

22. The method of claim 20, further comprising inputting crop-specific information and planting specifications, the remotely-sensed imagery, and meteorological data that includes the fine-resolution dynamical extended range weather forecast information.

23. The method of claim 22, wherein the crop-specific information includes a crop type and a variety of crop type determines a set of growth characteristics of the crop that enables the data processing modules to generate the profile of crop development, the set of growth characteristics including a timing to growth of each crop growth stage, nutrient requirements per crop growth stage, pest and disease susceptibility per crop growth stage, and one or more temperature thresholds for crop growth conditions.

24. The method of claim 22, wherein the meteorological data further includes observed weather data for a geographical area including the crop field, and current field-level weather data for the geographical area including the crop field, the observed weather data and the current field-level weather data being repetitively applied to the crop growth model during the time period where the crop maturity date has not yet been reached.

25. The method of claim 20, further comprising generating a crop summary report where the crop has reached maturity, and generating a crop growth and action report where the crop has not yet reached maturity.

26. The method of claim 20, further comprising generating a notification to a user when a validation of an estimate of crop growth stages identifies a change in the crop's growth, wherein the notification is provided to the user as a tactile indication on a mobile device.

27. The method of claim 20, further comprising providing the profile of crop development to a one or more application protocol interface modules each configured to generate an advisory service for agriculture management applications.

28. The method of claim 20, further comprising simulating a full growing season, prior to a beginning of a growing season, to project an expected timeline of crop growth stages and an anticipated crop maturity date.

* * * * *